United States Patent [19]

Staver

[11] 4,377,162
[45] Mar. 22, 1983

[54] FACIAL PROTECTIVE DEVICE, AND METHODS OF CONSTRUCTING AND UTILIZING SAME

[76] Inventor: Peter J. Staver, 1624 Detroit St., Lincoln Park, Mich. 48146

[21] Appl. No.: 210,740
[22] Filed: Nov. 26, 1980
[51] Int. Cl.³ ............................................. A61M 16/00
[52] U.S. Cl. ........................... 128/200.28; 128/207.13
[58] Field of Search ...................... 128/200.28, 200.27, 128/139, 207.13, 207.18, 205.25, 206.25, 206.24, 206.21

[56] References Cited

U.S. PATENT DOCUMENTS

| | | | |
|---|---|---|---|
| 428,592 | 5/1890 | Chapman | 128/200.27 |
| 2,792,000 | 5/1957 | Richardson | 128/201.15 |
| 2,831,487 | 4/1958 | Tafilaw | 128/207.18 |
| 2,843,122 | 7/1958 | Hudson | 128/207.13 |
| 2,921,581 | 1/1960 | Swearingen et al. | 128/206.25 |
| 3,357,426 | 12/1967 | Cohen | 128/206.25 |
| 4,231,363 | 11/1980 | Grimes | 128/206.28 |

FOREIGN PATENT DOCUMENTS

| | | | |
|---|---|---|---|
| 80647 | 6/1951 | Czechoslovakia | 128/200.28 |
| 30412 | 7/1964 | German Democratic Rep. | 128/204.21 |

*Primary Examiner*—Henry J. Recla
*Attorney, Agent, or Firm*—Irving M. Weiner; Pamela S. Burt; John L. Shortley

[57] ABSTRACT

A facial protective device for use in surgery and examination, adapted to extend outwardly from the base of the nose and be removably fixed in position by adhesive. The device and its adhesive adequately support surgical draping in a manner such as to ensure free passage of oxygen to the patient. Incorporated with the device is an oxygen delivery system which directs the oxygen most advantageously to the patient. The device is intended for single use and is disposable.

2 Claims, 8 Drawing Figures

U.S. Patent                Mar. 22, 1983                4,377,162
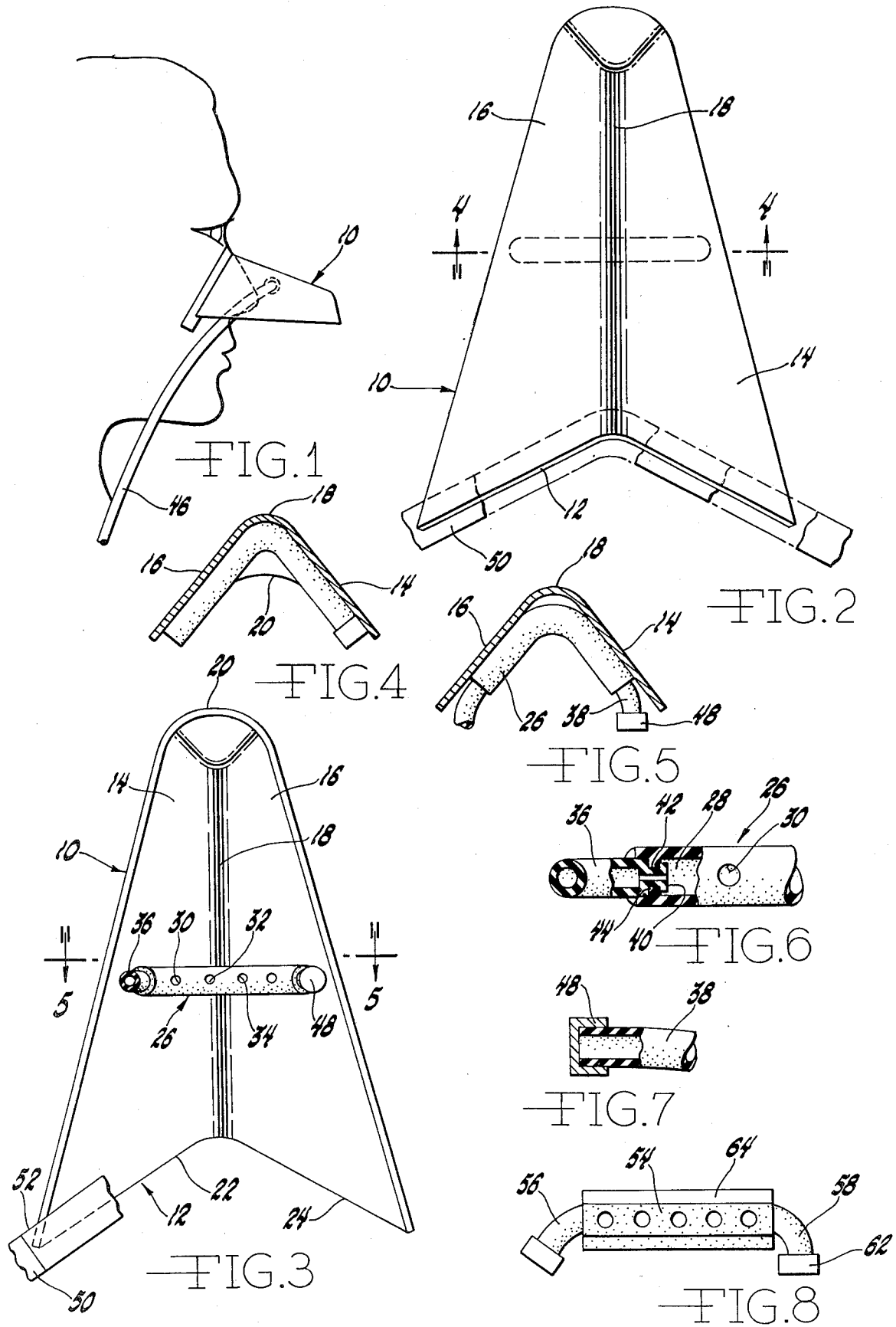

FACIAL PROTECTIVE DEVICE, AND METHODS OF CONSTRUCTING AND UTILIZING SAME

FIELD OF INVENTION

There are certain opthalmic operations which are very delicate and which require the use of optical instruments by the surgeons. If the surgeon is disturbed at all he is apt to be unable to find his previous location, i.e., the enlargement is so great that it is difficult to maintain concentration on the very minute field of view, and any disturbance is apt to lead to a need to start the whole operation over from scratch. It is also necessary to have as clear a field of vision as possible. If there are any devices auxiliary to the operation which must be placed near the eye they should be of minimum size and be as far from the eye as possible.

On the other hand, it is necessary that the surrounding area be masked off so as to have the maximum avoidance of the possibility of infection. Surgical drape, i.e., cloth, or a thin plastic sheet, is employed to cover the skin and mucous passages as much as possible.

It is also necessary that the patient have an adequate supply of oxygen. The patient is very often required to be awake during the operation. Disturbance of the flow of air to the patient would cause distress and the resulting possibility of movement of the patient or his eyes in an undesirable manner. Again, this is apt to interfere with the success of the operation.

Accordingly, it is necessary to provide some form of device which can be used to introduce oxygen to the patient, which can be positioned closely adjacent to the nose, and which could be useful as means of supporting the drapes without failing. Such a device should be fixedly secured to the patient, and should not move during the operation. Further, the device must also offer minimum interference with the line of vision of the surgeon, and must permit if not enhance the supply of adequate oxygen to the patient.

In an attempt to provide suitable masks or protective devices for such use, hospitals have been providing makeshift devices such as one formed of sheet aluminum foil. Often this foil is formed in the shape of half of a tepee. An adherent tape such as masking tape is secured to one end and the whole is then secured to the nose by the tape. This device works from time to time but on some occasions fails. Often when the tentlike member collapses the oxygen supply is not as desirable as it should be and the patient becomes uneasy. Again, this can interfere with the operation. It is impossible however to correct the situation without interference by the anesthetist with the covering provided by the drape material. In such case there can be soilage which is undesirable from the standpoint of the antiseptic situation desired, and there is the danger that the doctor's vision will be impaired.

DESCRIPTION OF PRIOR ART

U.S. Pat. No. 1,206,045 issued in 1916 to Smith entitled "NASAL INHALER" discloses an inhaler which has a casing formed of a metal or glass or other relatively rigid material. A groove extends around the edge of the casing and a plastic material in the form of a ring is secured to the metal casing by being pressed into the groove.

The casing with the plastic material is then applied to the nose of the patient and pressed with sufficient force so that the plastic material will conform to the contour of the nose and face. It is suggested that the pipes or the tubes through which the gasses are introduced may be sufficient for maintaining the mask in position since the tubes extend to the rear of the head. However, it is also stated that an elastic headband can be used or any other suitable means for holding the mask in place.

U.S. Pat. No. 2,859,748 issued in 1958 to Hudson, entitled "BREATHING MASK", discloses a breathing mask which is adapted to cover the nose. The mask comprises a shell, preferably constructed of some soft pliable materials. Polyethylene is mentioned, and in any event the material is to be relatively thin so as to be soft and flexible. It is contemplated that the mask will tend to mold itself to the face of the patient.

It is also contemplated that the mask will be of light weight and will be sufficiently low in cost so that it can be disposed of.

A strap is adapted to be used to hold the mask in place.

Oxygen is delivered by a tube. The tube is extended through a ring and an opening in the mask. The tube is of a greater diameter than these openings and thus is held in position by frictional contact with the peripheries of the openings. The air is directed towards the front of the mask so as not to bear directly upon the skin of the patient. Exhalation openings are provided.

U.S. Pat. No. 3,889,671 issued in 1975 to Baker, entitled "NASAL ADAPTER FOR ADMINISTERING ANALGESIC GAS" discloses a nasal mask which is constructed of a plastic material which can be sterilized and reused a number of times.

An air intake valve controlled by a valve control member and an expiration valve controlled by a second control are provided.

A sealing flange and a strap is used to securely position the adapter.

While these patents show masks for use in surgery, such as where an anethesia is required, they do not provide a protective device for the nose which will hold drape material, yet which will not interfere with the field of view required in certain opthalmic operations and will provide for an adequate supply of oxygen.

SUMMARY OF THE INVENTION

An object of this invention is to provide a breathing cone and facial protective device for use in opthalmic operations which will not interfere with the line of vision, which remains attached in the desired position, and which will provide a proper airway for the delivery of oxygen to the patient.

Further objectives of the invention are to provide a system that is universally adaptable to existing oxygen therapy systems and to ensure that a patient's nose and mouth are not inadvertantly covered by the sterile draping needed for the procedures.

An additional object is to provide a system for the intake of oxygen which will deliver the oxygen at a uniform rate and will spread the oxygen uniformily within the enclosure so as to avoid harsh concentrations.

It is also an aim to provide a throw-away type device, one that can be so inexpensively manufactured that it can be discarded. There will be no need to sterilize and re-use.

According to the invention there is provided a combined facial protective device and breathing chamber for use in opthalmic surgery comprising a material which is deformable at temperatures substantially above normal room temperatures, but is relatively rigid at lower temperatures. The material must be capable of being molded to a shape which will conform to the bridge of the nose and adjacent zygomatic arch of patients.

A preferred material is of a rubbery compound, such as of a PVC, which will retain a molded shape but which has some degree of flexibility. On the other hand, clear plastic which is available in sheet and tubular form and which can be molded at relatively low temperatures, such as 90° C., can be used though it might be relatively less flexible.

A pair of side panels extend upwardly from the base and from a central ridge also extending upwardly from the base. The side panels form a protective cover for the nose and a support for the drape material.

There is also provided a plenum chamber within the protective device spaced substantially forwardly of the base. The chamber has outlets directed toward the chin of a patient—outwardly of the ridge formed by the side panels. The plenum is positioned approximately midway along the ridge. Two inlet tubes are provided one at each end of the plenum. The anesthetist can thus introduce oxygen from either side. The inlet tubes can rotate, facilitating placement of the inlet conduit. A cap is provided for closing the unused inlet tube.

BRIEF DESCRIPTION OF THE DRAWINGS

FIG. 1 is a side elevation showing a protective device in accordance with the invention.

FIG. 2 is a top plan view of the protective device.

FIG. 3 is a bottom plan view.

FIG. 4 is a section taken along line 4—4 of FIG. 2.

FIG. 5 is a section taken along line 5—5 of FIG. 3.

FIG. 6 is a fragmentary partly sectional view of a plenum and a connector.

FIG. 7 is a fragmentary section showing an end cap for the connector of FIG. 6.

FIG. 8 is a bottom plan view of a modified form of plenum.

DESCRIPTION OF THE PREFERRED EMBODIMENTS

FIG. 1 illustrates a protective device and breathing mask according to the invention positioned on a patient about to have opthalmic surgery. A device according to the invention is designed to be fitted closely to the upper part of the bridge of the nose and then to extend upwardly and forwardly therefrom establishing approximately a thirty to forty degree angle between the device and the dorsum of the ridge of the nose and along the inferior orbital ridge to approximately the midpoint of the zygomatic arch.

As seen in FIGS. 2 and 3, in its preferred form the protective device 10 has a base 12 and a pair of side panels 14 and 16. The side panels extend upwardly and outwardly from the base 12 and merge to form an upper ridge 18. The panels also merge at the outer end, that is the end opposite the base 12 to form an outer rim 20.

The base 12 extends along the sloping ends 22 and 24 of the panels 14 and 16. The body of the device 10 is formed of material such as PVC or of a clear synthetic material. It can be made, for example, from sheet form acrylic material such as that available under the trademark Acrylite. According to the invention the material is of a nature that it can be readily shaped into the form shown in the drawings. Acrylic sheets for example can be molded when heated to about 200° F., i.e., about 94° C. Further, PVC as well as acrylic is relatively inexpensive, and it is intended that the device be of such a low cost that it can be readily disposed of after use. This will obviate the problems involved in resterilizing.

As seen in FIG. 1 and with reference to FIGS. 2 and 3, the device projects upwardly and forwardly of the nose to provide a protective cover as well as a chamber extending upwardly from the base of the ridge and facing downwardly towards the chin. Preferably the protective device and breathing mask has a length of 3½ to 4½ inches and its sloping edges 22 and 24 are of a length of about 1½ to 2 inches, thus defining a greater dimension of the device in a direction outwardly away from the patient's face than in the longitudinal direction of the patient's face.

Within the chamber formed by the mask, and substantially midway of its length there is provided a plenum chamber 26. This is in the form of a tube-like element preferably formed of the same material as the body 10, i.e., of PVC or an acrylic substance. The latter can be deformed when heated to a moderate extent, but will not deform when at normal room temperature, or at body temperature.

As seen in FIGS. 3 and 6, the plenum has a series of openings 30, 32 and 34. These are directed downwardly from the upper ridge 18 and in a direction such that when the device is positioned as shown in FIG. 1 the air stream will be directed towards the chin. As shown in FIGS. 3, 6 and 7, the tubular plenum 26 receives a pair of inlet tubes 36 and 38. These inlet tubes have bulbous ends 40 provided with a groove 42 and are each pressed into the chamber beyond a projecting ring 44 until the projecting ring 44, of plenum 26, is received within the respective groove 42. The inlet tubes can be swiveled within the rings 44 and thus the inlet tube angles can be altered. The inlet tubes may be made of a resilient material such as rubber.

By providing a pair of inlet tubes the anethetist can select from which side of the nose he prefers to introduce the oxygen into the plenum chamber. For this purpose a supply tube 46 (FIG. 1) is used, and this is adapted to frictionally receive the inlet tube end such as that of the end of tube 36. The unused inlet tube is provided with a cap 48 which frictionally engages the surface of the inlet tube such as 38, but which can be readily removed and placed on the opposite inlet tube 36.

In its preferred form the plenum and associated inlet tube and caps are provided as a single unit with the plenum already attached to the mask.

The device is removably attached to the patient by means of an adhesive. For this purpose an adhesive strip 50 is provided. The strip has adhesive on both sides protected by a cover paper such as 52. When the adhesive strip is to be used the adhesive on one side is exposed and the strip is attached to the inside of the panels 14 and 16 substantially adjacent base 12. Then when the device is to be applied to the patient, the paper on the opposite side is removed and the device is put into position and secured to the patient by the adhesive. The adhesive can be any one of several available adhesives, such as that employed on bandage strips, surgical drapes, masking tapes, etc. In fact, masking tape bearing adhesive on both sides can be used to adhere the device to the patient in operative position.

While in the preferred form shown in FIG. 3, the plenum is seen to be formed integrally with the panels 14 and 15, it is possible that the plenum can be supplied separately and attached after the side panels are molded. For this purpose the plenum shown in FIG. 8 can be supplied. In this case, the plenum 54 having the inlet tubes 56 and 58 and the caps 60 and 62 is provided with a base piece 64. After the side panels 14 and 16 are shaped as desired the plenum 54 is also molded to the desired shape and then attached to the panels by adhesives applied along the base 64.

The protective device in essence forms a covering for the nose that projects forwardly enough so as to ensure that the mouth is not covered by the draping material. The draping material is necessary in the operation in order to reduce the possibilities of infection. The oxygen is delivered within the protective device and directed outwardly and downwardly towards the chin so as not to irritate the nasal passages. The delivery tube 46 can be directed along the side on which it is least likely to be in the way. The ability to pivot the inlet tubes 36 and 38 facilitates placement of tube 46. It also makes it possible to rest tube 46 on the chin, thus putting less load on the mask.

The use of PVC, or a thermoplastic material such as sheet acrylic, contributes to producing a relatively inexpensive device. The use of a transparent material could facilitate use of the mask. The latter attribute might be helpful when the mask is being placed onto the patient.

The PVC and acrylic materials will be sufficiently rigid at temperatures prevalent during an operation to adequately support the drape material and the inlet tube. The heretofore used makeshift masks are weak in contrast. From time to time the latter fail, causing concern, and on occasions making it necessary to halt the procedure. If made of a relatively flexible material such as PVC or the like, the base 12 will tend to conform more exactly to the physiognomy of the patient.

The invention provides a semirigid barrier which projects substantially above the nasal passages and which will be rigid enough and reliable enough to support the draping material and the inlet supply tube 46 throughout the operation without failure. Thus, the operation can be conducted without interruption. A further advantage of the invention is that it is simply attached to the patient in the area of the zygomatic arch by adhesive. Further, the device is relatively inexpensive and can be disposed of after a single use.

While I have shown and described preferred forms of the invention it will be understood that other forms and variations can be devised within the scope of the invention and that accordingly the invention is to be limited only to the claims appended hereto.

I claim:

1. A protective device and breathing mask for use in opthalmic surgery comprising:
   a base formed generally in conformity with the bridge of a prospective patient's nose adjacent the zygomatic arch;
   a ridge extending from said base substantially centrally thereof;
   a pair of side panels extending from said base respectively on opposite sides of and structurally connected to said ridge and substantially forming two sides of a protective nose cover;
   a fluid plenum chamber within said device spaced substantially from said base;
   said plenum chamber being positioned approximately midway along said ridge;
   means for admitting air to said chamber;
   said chamber having outlets directed substantially downwardly from said ridge;
   means, operatively cooperating with said side panels, for removably securing said device to the face of a patient;
   said device having a greater dimension in a direction outwardly away from the face of a patient than in the longitudinal direction of the patient's face when said device is operably disposed on the patient; and
   said device being disposed substantially out of proximity with the eyes of the patient when said device is operably disposed on the patient.

2. A protective device and breathing mask for use in opthalmic surgery comprising:
   a base formed generally in conformity with the bridge of a prospective patient's nose adjacent the zygomatic arch;
   a ridge extending from said base substantially centrally thereof;
   a pair of side panels extending from said base respectively on opposite sides of and structurally connected to said ridge and substantially forming two sides of a protective nose cover;
   a fluid plenum chamber within said device spaced substantially from said base;
   means for admitting air to said chamber;
   said chamber having outlets directed substantially downwardly from said ridge;
   means, operatively cooperating with said side panels, for removably securing said device to the face of a patient;
   said device having a greater dimension in a direction outwardly away from the face of a patient than in the longitudinal direction of the patient's face when said device is operably disposed on the patient;
   said device being disposed substantially out of proximity with the eyes of the patient when said device is operably disposed on the patient;
   said device including a lower substantially open end extending outwardly from the face of the patient substantially above the upper lip when said device is operably disposed on the patient; and
   said ridge and said pair of side panels defining a substantially V-shaped cross section of said device.

* * * * *